United States Patent [19]

Fickel et al.

[11] 4,379,860

[45] Apr. 12, 1983

[54] POROUS, POWDERY POLYPROPYLENE

[75] Inventors: Walter Fickel, Erlenbach; Gerhard Ries, Obernburg, both of Fed. Rep. of Germany

[73] Assignee: Akzo NV, Arnhem, Netherlands

[21] Appl. No.: 279,045

[22] Filed: Jun. 30, 1981

[30] Foreign Application Priority Data

Jul. 15, 1980 [DE] Fed. Rep. of Germany ....... 3026762

[51] Int. Cl.$^3$ .............................................. C08J 9/26
[52] U.S. Cl. ...................................... 521/61; 521/56; 521/62; 521/143
[58] Field of Search ...................... 521/143, 56, 62, 61

[56] References Cited

U.S. PATENT DOCUMENTS

| 3,591,524 | 7/1971 | Eriksen | 210/924 |
| 3,681,237 | 8/1972 | Orban | 521/55 |
| 3,888,766 | 6/1975 | De Young | 521/54 |
| 4,187,187 | 2/1980 | Turbeville | 210/924 |

*Primary Examiner*—Morton Foelak
*Attorney, Agent, or Firm*—Michael J. Striker

[57] ABSTRACT

Process for the production of porous, powdery polypropylene, and utilization thereof. Hot solutions of polypropylene in pentaerythrol ester are slowly cooled down to approximately room temperature, forming a solidified mass, after which it is extracted with an extractant in which pentaerythrol is soluble. Before extracting, the size of the solidified mass may be reduced mechanically. After extracting, the pentaerythrol may be removed from the extractant to a high degree. Preferred embodiments include using solutions of polypropylene in pentaerythrol esters of fatty acids, more specifically, of synthetic fatty acids with 8-10 carbon atoms; using ethanol for the extraction; using solutions with a weight ratio of polypropylene to pentaerythrol ester of 30:70 to 10:90; having cooling of the solutions within the range of 260° to 120° C. proceed at an average rate of 1° to 20° C. per minute; using polypropylene with an admixture of up to 10% by weight of polyethylene. The porous, powdery polypropylene is characterized by an apparent density of 0.1 to 0.3 g/cm$^3$, a particle size of 50-700 μm, and an externally accessible porosity of 70-85%. The product may be used for the separation of hydrophobic substances from aqueous systems, in particular the separation of oil; for the adsorption of liquids, in particular, as oil adsorbent; as additive to paints, particularly to protective paints; and as carrier of substances for long-term release, in particular, odorants, and more specifically, as carrier of sexual attractants for insects.

11 Claims, No Drawings

POROUS, POWDERY POLYPROPYLENE

BACKGROUND OF THE INVENTION

The invention relates to porous, powdery polypropylene having a large internal surface accessible from the exterior and to processes for its production, as well as its utilization.

It is known how to produce polypropylene with a porous structure, particularly in the shape of compact structures such as sheets, but also in the shape of films, filaments and hollow filaments. U.S. Pat. No. 3,607,793, for instance, describe a process by which, proceeding from small polypropylene particles of a size from approximately 0.02 to 0.5 μm and dissolving these in hydrocarbons, porous films may be obtained if cooling is performed at a rate of less than 100° C. per minute.

This process, however, is not usable for the production of powdery, porous polypropylene. Considerable difficulties will arise, if transformation of porous structures obtained by the doctrine of U.S. Pat. No. 3,607,793 into powdery state is attempted by size reduction. On being ground, for instance, the material will, respectively, become viscous or begin to melt. A perfect porous, powder-like product can also not be obtained by intensive cooling, since the structures will be crunched and ruptured during the grinding process. Also, no powder with favorable particle size distribution can be obtained in this manner.

Also, compact masses of polypropylene with porous structure, as described in DE published application 2 737 745, can be pulverrized in this manner only under difficulties and will yield a powder having unsatisfactory properties in many respects.

Size reduction under liquid nitrogen will still not yield powders with fully satisfactory properties. Firstly, operating with liquid nitrogen is costly, as it is energy-intensive and the generation of gas in large quantities caused by evaporating nitrogen is noisome. Finally, the formation of fibrous edges at the cut or broken surfaces of the particulates, exerting an unfavorable effect upon the properties of the powder, e.g. its free-flowing qualities, cannot be avoided even by such intensive cooling as obtainable by using liquid nitrogen.

Porous, powdery substances may be used in the most different fields, e.g. in adsorption, as additives or fillers, or the like. The need exists therefore, for such porous substances, particularly those with improved properties, and also for appropriate production processes.

SUMMARY OF THE INVENTION

The object of the invention is, therefore, to make available porous, powdery polypropylene of suitable particle configuration and size distribution, having a large internal surface accessible from the exterior, a uniform pore structure, and good free-flowing qualities. The object of the invention is further an improved process for the production of such polypropylene powders, and, in particular, to enable economical and simple production. The object of the invention is, still further, to make evident particularly advantageous applications for such polypropylene powders.

These objects are attained by a process for the production of porous, powdery polypropylene, characterized by slowly cooling down to approximate room temperature, hot solutions of polypropylene in pentaerythrol ester, by, in given instances, mechanical size reduction of the solidified mass and by extraction of the latter with an extractant in which pentaerythrol is soluble and, in given instances, by the solvent subsequently being removed to a high degree. Preference is given herein to using solutions of polypropylene in esters of pentaerythrol and fatty acids, particularly synthetic fatty acids with 8 to 10 carbon atoms.

Ethanol is particularly suitable for extracting pentaerythrol ester. It will be favourable to perform the process by using solutions of a weight ratio polypropylene: pentaerythrol of approximately 30:70 to 10:90, preferably 25:75 to 15:85. Cooling of the solutions in the range from approximately 260°-120° C., should, suitably, ensue at an average rate of approximately 1° to 20° C. per minute, preferably at a rate of 2° to 10° C. per minute. Up to 10% polyethylene may be admixed to the polypropylene. The object of the invention is, furthermore, porous, powdery polypropylene, characterized by particles of a diameter from 50–700 μm, an apparent density of 0.1 to 0.3 g/cm$^3$, and an externally accessible porosity from 70 to 85%. The apparent density will preferably be 0.13–0.15 g/cm$^3$, the particle size preferably 50 to 150 μm.

The object of the invention is, furthermore, the utilization of porous, powdery polypropylene in separating hydrophobic substances, particularly oil, from aqueous systems, as well as in the adsorption of liquids, wherein the properties as oil adsorbent merit particular emphasis. Powdery polypropylene according to the invention, may be used with great advantage as additive to paints, particularly as additive to protective paints.

It is, furthermore, very suitable as carrier of substances for long-term releasing.

For the production of the porous, powdery polypropylene according to the invention, one will, in general proceed in the manner that, by the method as usual per se, a solution of polypropylene and pentaerythrol ester is produced by heating to temperatures of approximately 250°-260° C.

A polypropylene obtained by the usual production methods, may be used herein as polypropylene. Particularly suitable will be polypropylene of a medium, higher, or also lower, molecular weight. Commercial types, e.g. Hostalen 1070, may be used.

The polypropylene may be used by itself or in a mixture with other polymers or other additives. The polypropylene may be cut back herein with a larger or smaller quantity, e.g. 50%, of one or a plurality of other polymers. Polypropylene types of different molecular weights may also be intermixed; the use of copolymers is, of course, permissible.

It will be particularly advantageous if up to 10% polyethylene are admixed to the polypropylene. The polyethylene may, therein, be high-density or low-density polyethylene.

Varying the molecular weights of the polypropylene used herein will allow influencing the particle size of the powder. Increasing the melting index of the polypropylene will serve to lower the particle size, particularly that of the so-called primary granules.

It appears that the invention will serve to, so to speak, preprogram the particle size in a very favorable manner, so that the individual particles are obtained less by splitting up, i.e. by destruction of larger units, but rather by a separating process which, of course, may be preceded by mechanical breaking-up processes such as cutting or grinding.

A very favorable particle distribution may, according to the invention, be obtained with the product available on the day of application from Chemische Werke Hüls, Marl, and designated Vestolen PV 3377.

To prepare the solutions, usual, commercially available pentaerythrol esters may be used as solvent. A very suitable product is the commercially available product, distributed on the day of application by the firm of Henkel & Cie., Düsseldorf, under the product designation BK 2104.

Particularly suitable are pentaerythrol esters obtained from pentaerythrol and monocarboxylic acids, i.e. fatty acids, synthetic fatty acids in particular, with 8 to 10 carbon atoms. Pentaerythrol is a known, readily available quadrivalent alcohol of the formula

$C(CH_2OH)_4$.

The solution obtained by heating polypropylene and pentaerythrol ester is then filled into a vessel or other container and cooled at the appropriate rate. The solution may also be cast in appropriate thickness onto a metallic sheet or belt, with requisite cooling obtained by the selection of the thickness of the layer or, in given instances, cooling of, respectively, the sheet or belt. Also, drums, such as cooling drums or rolls may be used as substrate for the cast solution.

After cooling, a solid mass of friable consistence is obtained which may readily be removed from the substrate, e.g. by stripping and which may readily be reduced in size by impact or crumbling.

This mass is then admitted to extraction with a solvent which will dissolve pentaerythrol ester but not, however, polypropylene. Exemplary for this are: alcohols such as methanol, ethanol, isopropanol and butanol, acetone, acetic acid ethyl ester, benzene, toluene, xylene, methylene chloride, chloroform and carbon tetrachloride.

Particularly suitable for the aforesaid purpose is ethanol.

It is recommended to stir during the extraction process, since extraction is enhanced thereby and a size reduction into smaller particles will concomitantly ensue. Extraction is continued until the pentaerythrol has been separated to an adequate degree.

The powder may be dried after extraction, e.g. heating it in an oven by treating it with dry air. Separation of the extractant will preferably take place in a vacuum, excessive heating of the particles being avoided thereby. It will be suitable in many instances, not to heat the powder to above 50° C. Also, in many instances, it will suffice that the extractant is removed save for a remnant and made available for certain applications, e.g. with alcohol-produced moisture.

It was particularly unexpected, that powdery polypropylene of a very favorable particle size distribution could be obtained in this manner. According to the invention, it will be possible to obtain a powder with its particle sizes mainly in the range from 50 to 700 µm, wherein the range from 50 to 150 µm is preferred. The distribution may be kept within very narrow limits.

It is practicable to influence particle size distribution by varying the cooling conditions, by the choice of the molecular weight and the polypropylene, and by suitable additives.

The powder may readily be screened and, in given instances, separated into different particle size fractions. The powder as obtained, is distinguished by a large internal surface well accessible from the exterior, which will manifest itself particularly by excellent adsorption properties relative to the most different substances and which, on the other hand, will allow, respectively, saturation or charging of the powder with the most different substances, with the latter, in turn, being released to the exterior in the course of time.

The porosity, relative to the powder weight, is very high and will amount to several $cm^3$ per gram, e.g. 3.2 $cm^3/g$.

It was particularly unexpected, that the porous powders according to the invention, are in an outstanding manner suitable for the separation of hydrophobic substances from water, with the capacity for separating oil from water meriting special emphasis. It is thus practicable by treatment with porous polypropylene powder, e.g. by introducing powder according to the invention and stirring, to perform, respectively, purification or after-purification of water that has been prepurified but is still affected to a limited degree by contamination, as evidenced by a rainbow-hued colored film on the water, so that the colored film will disappear in consequence of such treatment.

Using the powders according to the invention, will allow adsorbing considerably greater quantities of liquid, oil in particular, than is the case with the known products. It is thus possible with one liter of porous, powdery polypropylene according to the invention, to adsorb 0,82 liter, and even 1,19 liters of fuel oil. The adsorbance of the powder is outstanding. The powder need merely be sprinkled onto puddles of oil and this will, within a short time, result in the oil being adsorbed by the powder. The porous, powdery masses according to the invention, may be produced with a very low apparent specific gravity. Their specific adsorbance is very high.

The porous, powdery masses are, furthermore, suitable in an outstanding manner as additive to the most different paints. Since, according to the invention, a very fine granulation is obtainable, the powders allow very good dispersion in the paints, so that very homogeneous paints can be obtained, which may be used without problems.

Due to their large internal surface and the great internal volume well accessible from the exterior, the powders invention may be filled with the most different substances which may then, spread over longer periods of time, escape back to the exterior. Appropriate size adjustment of pore structure and interior volume will enable influencing the long-term release also in respect of time. Active substances may be incorporated into porous substances used as additives for paints, said active substances then exerting a corresponding activity in the paint for a long time. Particularly suitable for this purpose are fungicides, algae inhibitors, fungicidous substances and anti-corrosion agents. These types of protective paints are particularly suitable for the coating of ship hulls which, as is known, are exposed to very strong corrosion and algae infestation, et cetera.

The powder according to the present invention is particularly suitable as carrier for long-term release also in the fields of agriculture and forestry. It may be charged with the most different substances and then be distributed onto the soil or plants. In this manner, pest control agents, trace elements, may be introduced and dispersed in dosages, and it is also practicable to disperse in the powder odorants such as sexual attractants, so-called pheromones, by which male insects are attracted or confused and insemination of females prevented thereby.

The extractant may conveniently be recovered, particularly when using ethanol.

The process according to the present invention is unobjectionable as to toxicology, so that no concern need exist in respect of the operating personnel becoming exposed to any hazards during the process. The extracted pentaerythrol ester may readily be used again, so that also no environmental pollution is to be expected.

The process is of extreme economy in operation and makes available a powdery product from an inexpensive polymer.

The novel features which are considered as characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

EXAMPLE 1

500 g of a mixture of 90% polypropylene and 10% polyethylene (commercial product of firm Chemische Werke Hüls, Marl, designation Vestolen PV 3377) are dissolved with stirring at 250°–260° C. in 2000 g of a commercially available pentaerythrol ester (BK 2104 of firm Henkel & Cie., Düsseldorf). As soon as a homogenous solution has been obtained (approximately after 2–3 hours), the liquid is cast in an approx. 5 mm thick layer onto a stainless-steel sheet.

After cooling, the solidified friable mass is washed 10×30 mins with 5 L ethanol each, to remove the pentaerythrol ester. The fine-pored Vestolen powder, separated by a filter, is dried in a layer of approx. 3 cm thickness on a grating, under a vacuum and at 40°–50° C.

EXAMPLE 2

Into 5600 g of pentaerythrol ester, identical to that of example 1, 240 g of a commercially available polypropylene (Hostalen 1070 granulate-commercial product of Hoechst AG), are introduced under stirring and dissolved within approx. 3 hours at 260° C. Upon having attained a homogenous solution, the latter is cast upon a cold metallic sheet. After the solution has solidified into a friable mass, the latter is washed 10×30 mins with 12 L ethanol each, to remove the pentaerythrol ester.

The Hostalen powder, siphoned off through a vacuum filter, is dried in vacuum as described under Example 1.

It will be understood that each of the elements described above, or two or more together, may also find a useful application in other types of powder productions differing from the types described above.

While the invention has been illustrated and described as embodied in a process for the production of porous, powdery polypropylene, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. Process for the production of porous, powdery polypropylene, comprising slowly cooling down to approximate room temperature, hot solutions of polypropylene in pentaerythrol ester, thereby forming a solidified mass, and extracting the solidified mass with an extractant in which pentaerythrol is soluble.

2. Process according to claim 1, using solutions of polypropylene in pentaerythrol esters of fatty acids.

3. Process according to claim 2, using pentaerythrol esters of synthetic fatty acids with 8 to 10 carbon atoms.

4. Process according to claim 1, characterized by using ethanol for the extraction.

5. Process according to claim 1, characterized by using solutions with a weight ratio of polypropylene to pentaerythrol ester of 30:70 to 10:90.

6. Process according to claim 5, using solutions with a weight ratio of polypropylene to pentaerythrol ester of 25:75 to 15:85.

7. Process according to claim 1, wherein said cooling of the solutions, within the range of 260° to 120° C., proceeds at an average rate of 1° to 20° C. per minute.

8. Process according to claim 7, wherein cooling proceeds at a rate of 2° to 10° C. per minute.

9. Process according to claim 1, using polypropylene with an admixture of up to 10% by weight of polyethylene.

10. Process according to claim 1, further comprising before said extracting, mechanically reducing the size of the solidified mass.

11. Process according to claim 1, further comprising after said extracting, removing the pentaerythrol from said extractant to a high degree.

* * * * *